United States Patent [19]
Anderson

[11] 3,942,898
[45] Mar. 9, 1976

[54] DENSITOMETER FOR MEASURING THE DENSITY OF AN OPTICAL ELEMENT SUCH AS A FILM BADGE

[75] Inventor: Robert J. Anderson, Villa Park, Calif.

[73] Assignee: Beckman Instruments, Inc., Fullerton, Calif.

[22] Filed: July 25, 1974

[21] Appl. No.: 491,876

[52] U.S. Cl. ............... 356/202; 250/559; 356/204; 356/205
[51] Int. Cl.² ...................................... G01N 21/22
[58] Field of Search ........... 356/201, 202, 203, 204, 356/205, 206; 250/559, 571

[56] References Cited
UNITED STATES PATENTS
3,765,778  10/1973  Bey et al. ............................ 356/202
3,807,875  4/1974   Fisher et al. ....................... 356/201

Primary Examiner—Vincent P. McGraw
Attorney, Agent, or Firm—R. J. Steinmeyer; R. R. Meads

[57] ABSTRACT

A densitometer for providing an output which is a function of the density of a film badge in a photodosimeter system. The light passing through the film badge is received by a photodiode which generates a current signal which is directly proportional to the intensity of the received light. The current signal is converted to a voltage signal, the converting means being biased so that the voltage signal is zero when no light is received by the photodiode. The voltage signal is applied, together with a reference voltage, to a log-ratio circuit which generates an output signal proportional to the log of the ratio of the reference voltage to the voltage signal, the output of the log-ratio circuit being displayed. A circuit is operative, when the film badge is removed from the light path, to adjust the reference voltage until the output of the log-ratio circuit is zero.

9 Claims, 3 Drawing Figures

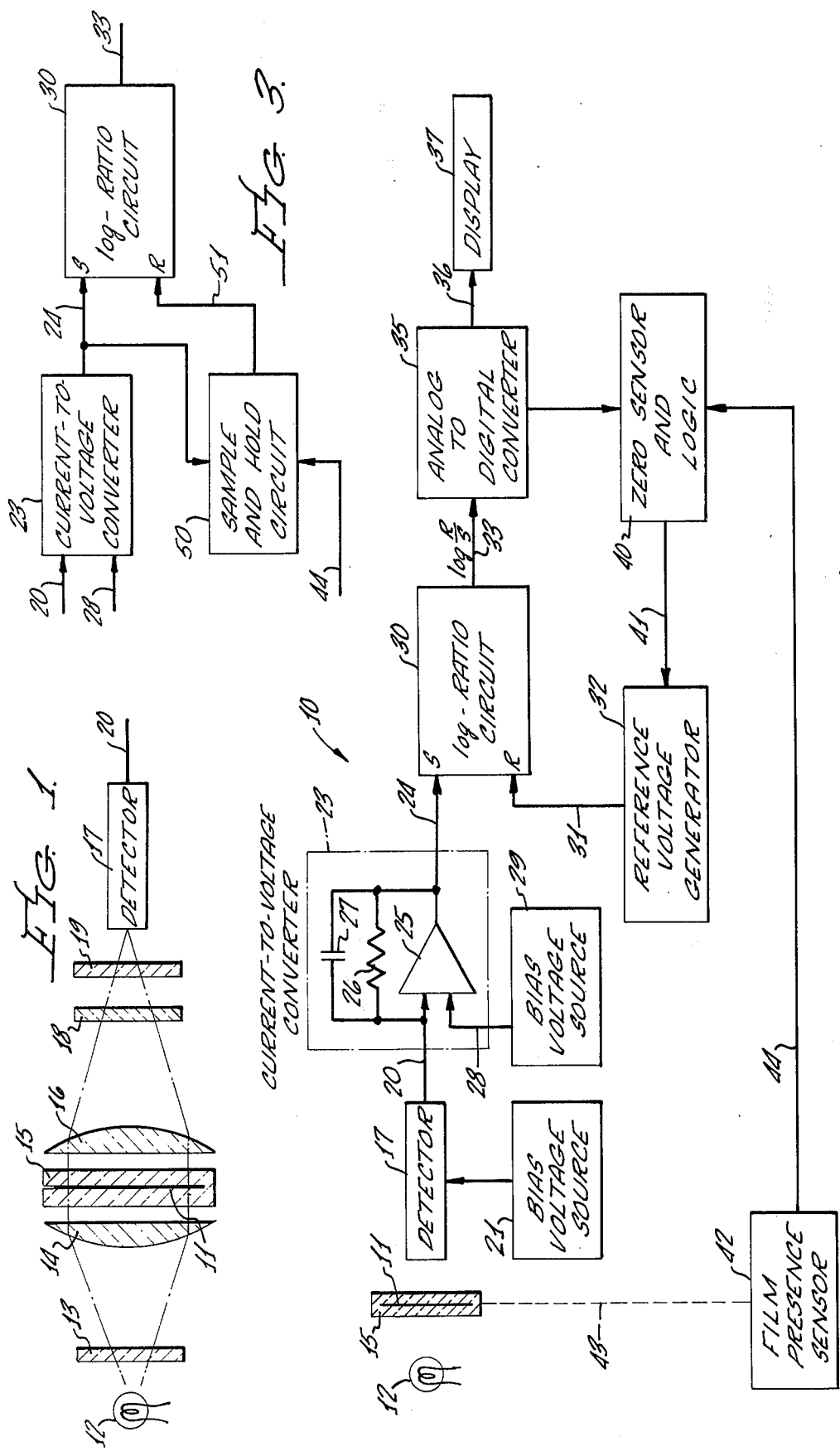

DENSITOMETER FOR MEASURING THE DENSITY OF AN OPTICAL ELEMENT SUCH AS A FILM BADGE

BACKGROUND OF THE INVENTION

1. Field of the Invention.

The present invention relates to a densitometer and, more particularly, to a densitometer for use in a photodosimeter system having a high degree of accuracy over a wide range of measurements.

2. Description of the Prior Art.

In my copending application Ser. No. 491,875, filed concurrently herewith, for Photodosimeter Film Badge, there is disclosed a photodosimeter film badge sensitive to non-ionizing radiation which is useful during phototherapy for the treatment of hyperbilirubinemia in the newborn. Such film badge is capable of permitting the measurement of the total irradiance effective in decomposing bilirubin. The film badge undergoes an optical density change as a result or irradiation by the phototherapy lamps and such density change is directly proportional to the time interval of the irradiance. The optical density change occurs very slowly so that the film badge is responsive to phototherapy irradiance over periods extending from a few hours to as many as 96 hours.

Since the optical density of the film changes irreversibly as a function of irradiance, such optical density may be measured directly without any chemical processing of the film. This permits exposure to be monitored continuously. However, in order to derive the full benefits of the film badge of my copending application, it is necessary to be able to measure density extremely accurately, over a wide range of densities.

More specifically, phototherapy for the treatment of hyperbilirubinemia in a newborn typically continues for a minimum of a few hours and a maximum of four days (96 hours). With an irradiance level of approximately 1 $mW/cm^2$, there is a total exposure, over a period of 100 hours, of approximately 360 joules. Any system used for measuring exposure must measure to an accuracy of about 15 minutes in an exposure interval of 100 hours, requiring an accuracy of about 0.25 percent, or about 1 part in 400. Since the film badge of my copending application exhibits a total density change of about 3.000 in a 100 hour interval, such an accuracy implies that a density change of 0.008 must be accurately measured. Thus, any densitometer must be extremely accurate, the output reproducible, and it must operate over a wide range of densities. However, while many commercial densitometers are available at prices ranging from several hundred to several thousand dollars, no reasonably priced densitometer meets these requirements.

SUMMARY OF THE INVENTION

According to the present invention, there is provided a densitometer for use in a photodosimeter system meeting all of the requirements specified above. The present densitometer is capable of providing an accuracy of 1 part in 4,000 or 0.001 density units over a density range of 4.000. The output of the present densitometer is reproducible and it operates over a wide range of densities. The present densitometer incorporates an automatic mechanism which insures that at a density of zero, the displayed output is also zero.

Briefly, the present densitometer for providing an output which is a function of the density of a film badge or other optical element comprises: a source of light; means for holding the film badge in the path of the light, the film badge transmitting an amount of light which is inversely proportional to the density thereof; a photodiode positioned to receive the light transmitted through the film badge for generating a current signal which is directly proportional to the intensity of the received light, the current signal having a non-zero value when no light is received by the photodiode; means responsive to the photodiode for converting the current signal to a voltage signal which is directly proportional to the intensity of the received light; means for biasing the current-to-voltage converting means so that the voltage signal is zero when no light is received by the photodiode; means for generating a reference voltage; circuit means responsive to the voltage signal and the reference voltage for generating an output signal proportional to the log of the ratio of the reference voltage to the voltage signal, the output signal being proportional to the density of the film badge; means for displaying the output signal; means for adjusting the reference voltage until the output signal is zero; and means for sensing the presence of the film badge in the holding means for disabling the adjusting means when the film badge is present.

OBJECTS

It is therefore an object of the present invention to provide a densitometer.

It is a further object of the present invention to provide a densitometer for use in a photodosimeter system having an accuracy of at least 1 part in 400.

It is a still further object of the present invention to provide a densitometer having a reproducible output capable of accurately measuring density over a wide range of densities.

Still other objects, features, and attendant advantages of the present invention will become apparent to those skilled in the art from a reading of the following detailed description of the preferred embodiment constructed in accordance therewith, taken in conjunction with the accompanying drawings wherein like numerals designate like parts in the several figures and wherein:

BRIEF DESCRIPTION OF THE DRAWINGS

FIG. 1 is a diagramatic view of the optical geometry of the present densitometer;

FIG. 2 is a block diagram of a densitometer constructed in accordance with the teachings of the present invention; and FIG. 3 is a block diagram of a possible modification to the densitometer of FIG. 2.

DESCRIPTION OF THE PREFERRED EMBODIMENT

The film badge disclosed in my beforementioned copending patent application is responsive to the irradiance effective in decomposing serum bilirubin. The film badge disclosed therein initially has a density of between 3 and 4, thereby initially transmitting only a small amount of the light incident thereon. As the film badge continues to be exposed by the illumination used during phototherapy for the treatment of hyperbilirubinemia, the density decreases at a wavelength of approximately 455 nanometers. This decrease in density is directly proportional to exposure and must be measured to provide a useful output.

The present densitometer, generally designated 10, is designed to provide an output which is a function of the density of a film badge, generally designated 11, or any other optical element, in a very narrow wavelength interval in the vicinity of 455 nm. Thus, and with reference to FIG. 1, densitometer 10 includes a lamp 12 which is typically a high efficiency tungsten lamp with a built-in parabolic reflector, since such a lamp provides a light output in the frequency spectrum of interest. The output of lamp 12 passes through a first filter 13 which passes blue light and blocks visible and infared light. Filter 13 is typically a blue glass filter. The light passing through filter 13 is collimated by a lens 14 and conducted to a film holder 15 capable of holding film badge 11 perpendicular to the collimated rays. This technique is used so as to illuminate the entire area of film badge 11, which increases the accuracy of densitometer 10 when the density of film badge 11 is high and only a small amount of light passes therethrough.

The light transmitted through film badge 11, which is inversely proportional to the density thereof, is focused by a second lens 16 onto a detector 17. Interposed between lens 16 and detector 17 is a second blue glass filter 18 designed to block stray light. Interposed between filter 18 and detector 17 is a bandpass filter 19 having a very narrow passband, on the order of 5 – 10 nm, in the vicinity of 455 nm. Detector 17 generates a signal on a line 20 which is directly proportional to the intensity of the received light. Thus, this signal is inversely proportional to the density of film badge 11 in the vicinity of 455 nm.

Referring now to FIG. 2, detector 17 may be any wellknown light responsive device for generating a signal proportional to the light incident thereon. On the other hand, it should be recognized that since the initial density of film badge 11 is quite high, the amount of light transmitted to detector 17 will be quite low and the output of detector 17 will also be quite small. Therefore, it is important that the output signal from detector 17, when no light is received thereby, be quite small since fluctuations therein as a result of noise will effect the accuracy of densitometer 10. With this in mind, detector 17 is preferably a vacuum photodiode, such as RCA Model 1P42. Such a photodiode acts as a current source which generates a current signal which is directly proportional to the intensity of the received light.

Densitometer 10 also includes a bias voltage source 21 which applies a suitable bias voltage to the photodiode in detector 17. By properly selecting the value of the bias voltage, the current from detector 17 when no light is received thereby may be minimized. When an RCA 1P42 vacuum photodiode is used, the value of bias voltage source 21 is preferably 15 volts.

The output of detector 17, on line 20, is applied to a current-to-voltage converter 23 which converts the current signal from detector 17, on line 20, to a voltage signal, on line 24. Furthermore, current-to-voltage converter 23 operates such that the voltage signal on line 24 is zero when no light is received by detector 17. More specifically, current-to-voltage converter 23 preferably includes a conventional operational amplifier 25 having a conventional feedback resistor 26 and also a feedback capacitor 27 for integration to eliminate noise. The output of detector 17, on line 20, is applied to one input of operational amplifier 25 whereas the other input, which is normally grounded, receives, over a line 28, the output of a bias voltage source 29. The bias voltage provided by source 29 is adjusted so that the output of operational amplifier 25, on line 24, is zero when no light is received by detector 17. This may be achieved, very simply, by covering detector 17 so that no light is received thereby and by adjusting bias voltage source 29 until the output of operational amplifier 25 reaches zero.

The output of converter 23 is now a voltage signal which is zero when no light is received by detector 17 and which increases as the intensity of the light incident on detector 17 increases. Thus, the voltage signal on line 24 is directly proportional to the transmittance of film badge 11. However, since exposure, the desired quantity, is a function of density, rather than transmittance, the output of converter 23 is applied to the signal input (S) of a log-ratio circuit 30. That is, density $(D) = -\log T$, where $T$ = transmittance, and circuit 30 performs this mathematical operation. More specifically, since $T = (S/R)$, $D = -\log (S/R)$ or $\log (R/S)$. Log-ratio circuit 30 receives, at its reference input $(R)$, a signal over a line 31 from a reference voltage generator 32. Log-ratio circuit 30 is a conventional circuit for generating an output signal, on a line 33, which is proportional to the log of the ratio of the reference input to the signal input.

As will be explained more fully hereinafter, the value of the reference voltage from generator 32 may be adjusted to provide a zero output signal when the density of film badge 11 is zero. Thereafter, as the density of film badge 11 increases, the output of log-ratio circuit 30, on line 33, will increase proportionately.

Initial zero adjustment of the output of log-ratio circuit 30 may be achieved simply by removing film badge 11 from holder 15 so that the light incident on detector 17 is indicative of a density of zero. At this time, the output of reference voltage generator 32 may be adjusted to yield a zero output from circuit 30. Full-scale calibration of circuit 30 is achieved by blocking all light to detector 17 so that the output of converter 23, on line 24, is zero. The internal elements of log-ratio circuit 30 may then be adjusted to provide the desired output. Thereafter, as the density of film badge 11 varies between its minimum and maximum values, the output of log-ratio circuit 30, on line 33, will vary proportionately.

In order to display density to the desired degree of accuracy, the output of log-ratio circuit 30, on line 33, is applied to a twelve-bit analog-to-digital converter 35 which generates a digital output, on a line 36, having an accuracy of 1 part in 4,000, representing 0.001 density units over a density range of 4.000. This output is applied to a digital display device 37 capable of displaying four digits.

It is obvious that densitometer 10 will continue to provide an accuracy of 1 part in 4,000 only as long as the circuit elements do not vary in value by a greater amount. However, in practice, this will not occur and display 37 cannot continue to generate an output of 0.000 for any length of time with film badge 11 removed from holder 15. Therefore, according to the preferred embodiment of the present invention, the output of analog-to-digital converter 35 is applied to a feedback circuit, generally designated 40, the output of which is applied over a line 41 to reference voltage generator 32 to adjust the value of the voltage output thereof until the signal output from converter 35 is zero. More specifically, feedback circuit 40 would be a conventional logic circuit for sensing when the output of converter 35 is different from zero and whether such difference is positive or negative. Circuit 40 would then apply a suitable signal over line 41 to signal generator 32 to cause generator 32 to make an appropriate adjustment in its output voltage to reduce such difference to zero. This check of the output of converter 35 would be repeated regularly and if the zero level changes, an increased or decreased potential is applied to the reference input of circuit 30 to drive the output of converter 35 back to zero. Thus, any variations in circuit values with time will be automatically cancelled.

Obviously, circuit 40 operates only when film badge 11 is removed from holder 15 since only at that time is the output of converter 35 zero. Therefore, to disable circuit 40 when a film badge 11 is inserted into holder 15, dosimeter 10 includes a circuit 42, which is mechanically connected to holder 15, as shown at 43, for sensing when film badge 11 is inserted into holder 15. When film badge 11 is inserted, sensor 42 generates a signal on a line 44 which is applied to zero sensor 40 to disable same.

It will be apparent to those skilled in the art that the output of log-ratio circuit 30 will be zero only when the output of reference voltage generator 32 is equal to the output of converter 23, thereby equalizing the values of the inputs to circuit 30. Therefore, the output of converter 23 itself may be used to provide a reference voltage when film badge 11 is removed from holder 15. More specifically, and with reference now to FIG. 3, the output of current-to-voltage converter 23, on line 24, may be applied not only to the signal input of log-ratio circuit 30 but also to the input of a sample and hold circuit 50, the output of which is applied, over a line 51, to the reference input of circuit 30. This permits the complete elimination of reference voltage generator 32 and feedback circuit 40. However, under these circumstances, the output of film presence sensor 42, on line 44, is applied to sample and hold circuit 50.

In operation, when film badge 11 is removed from holder 15, as sensed by circuit 42, circuit 50 operates to sample and hold the output of converter 23 and to apply such output to the reference input of circuit 30. Thus, circuit 50 generates a reference signal on line 51 which is automatically equal to the signal input to circuit 30 by virtue of the fact that it is, in fact, the same signal. Therefore, with film badge 11 removed from holder 15, the output of circuit 30 remains zero in spite of fluctuations in the voltage on line 24.

On the other hand, the hold capability of circuit 50 is required when an actual density measurement is being made. That is, when film badge 11 is inserted into holder 15, the signal on line 44 from film presence sensor 42 causes circuit 50 to open the connection between lines 24 and 51 and, thereafter, to apply the held voltage value to line 51. This held voltage thereby acts as the reference voltage. In addition, as soon as film badge 11 is removed from holder 15, such held voltage value is adjusted, as necessary, with fluctuations over line 24.

While the invention has been described with respect to a preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

I claim:

1. A densitometer for providing an output which is a function of the density of an optical element such as a film badge comprising:
    a source of light;
    means for holding said optical element in the path of said light, said optical element transmitting an amount of light which is inversely proportional to the density thereof;
    detector means positioned to receive the light transmitted through said optical element for generating a first signal which is directly proportional to the intensity of the received light;
    means for generating a reference signal;
    circuit means responsive to said first signal and said reference signal for generating a second signal proportional to the log of the ratio of said reference signal to said first signal, said second signal being proportional to the density of said optical element;
    means for displaying said second signal; and
    means operative when said optical element is removed from said light path for adjusting said reference signal until said second signal is zero.

2. A densitometer according to claim 1 wherein said detector means is a vacuum photodiode.

3. A densitometer according to claim 2 wherein said first signal is a current signal having a non-zero value when no light is received by said photodiode and further comprising:
    means responsive to said photodiode for converting said current signal to a voltage signal which is directly proportional to the intensity of the received light; and
    means for biasing said current-to-voltage converting means so that said voltage signal is zero when no light is received by said detector means.

4. A densitometer according to claim 3 wherein said current-to-voltage converting means comprises:
    an operational amplifier receiving said current signal at one input thereof; and wherein said biasing means comprises:
    means for generating a bias voltage, said bias voltage being applied to another input of said operational amplifier to bias same.

5. A densitometer according to claim 3 wherein said reference signal generating means generates a reference voltage and wherein said second signal is proportional to the log of the ratio of said reference voltage to said voltage signal.

6. A densitometer according to claim 1 further comprising:
    means for sensing the presence of said optical element in said holding means and for disabling said adjusting means when said optical element is present.

7. A densitometer according to claim 1 wherein said display means is a digital display and further comprising:
    means interposed between said circuit means and said display means for converting said second signal into a digital signal.

8. A densitometer according to claim 1 further comprising:
    a 12-bit analog-to-digital converter interposed between said circuit means and said display means for converting said second signal into a digital signal having an accuracy of 1 part in 4,000; and wherein said display means comprises:

a four digit digital display.

9. A densitometer according to claim 1 wherein said reference signal generating means comprises:

circuit means responsive to said first signal for sampling and holding the value thereof and for applying said held value to said log-ratio circuit means; and wherein said adjusting means comprises:

means for sensing the presence of said optical element in said holding means and for generating a signal indicative thereof, said signal being applied to said sample and hold circuit means, said sample and hold circuit means being operative, when said optical element is removed from said holding means, to update the sampled and held value of said first signal.

* * * * *